United States Patent [19]
Daikuzono

[11] Patent Number: 4,592,353
[45] Date of Patent: Jun. 3, 1986

[54] MEDICAL AND SURGICAL LASER PROBE

[75] Inventor: Norio Daikuzono, Ichikawa, Japan

[73] Assignee: Surgical Laser Technologies Ohio, Inc., Cincinnati, Ohio

[21] Appl. No.: 612,674

[22] Filed: May 22, 1984

[51] Int. Cl.⁴ .............................................. A61B 17/36
[52] U.S. Cl. .............................. 128/303.1; 219/121 L; 219/121 LR
[58] Field of Search ........ 128/303.1, 303.17, 395–398; 219/121 L, 121 LP, 121 LQ, 121 LR

[56] References Cited

U.S. PATENT DOCUMENTS

| 3,236,707 | 2/1966 | Lins | 219/121 LP |
|---|---|---|---|
| 3,821,510 | 6/1974 | Muncheryan | 128/303.1 |
| 3,843,865 | 10/1974 | Nath | 128/395 |
| 3,858,577 | 1/1975 | Bass et al. | 128/303.17 |
| 4,069,080 | 1/1978 | Osborne | 219/121 LR |
| 4,233,493 | 11/1980 | Nath | 219/121 L |
| 4,270,845 | 6/1981 | Takizawa et al. | 128/303.1 |
| 4,273,109 | 6/1981 | Enderby | 128/303.1 |
| 4,313,431 | 2/1982 | Frank | 128/303.1 |
| 4,448,188 | 5/1984 | Loeb | 128/303.1 |

FOREIGN PATENT DOCUMENTS 8202604  8/1982  PCT Int'l Appl. .............. 128/303.1

Primary Examiner—William E. Kamm
Assistant Examiner—Ruth S. Smith
Attorney, Agent, or Firm—McDougall, Hersh & Scott

[57] ABSTRACT

A medical and surgical laser probe which is provided with a contact member made of a laser transmitting material in front of a forward end of a laser guide so as to enable the probe to be used in contact with the tissue. The contact member has a specified configuration which causes no substantial convergency so as to be specially adapted coagulation treatment. With the contact member of the present invention, the coagulation treatment can be carried out effectively.

9 Claims, 10 Drawing Figures

MEDICAL AND SURGICAL LASER PROBE

BACKGROUND OF THE INVENTION

This invention relates to a medical and surgical laser probe, and more particularly to a medical and surgical laser probe having, at a forward end thereof, a contact member made of a laser transmitting material so as to allow the probe to be used in contact with the tissue which is to be subjected to laser irradiation treatment.

There has already been developed and practically used a non-contact type laser irradiation probe made of an optical fiber for carrying out incision and coagulation of the tissue for a living organ through irradiation of laser beam emitted from the optical fiber. This type of laser probe makes incision or coagulation by irradiating laser beam such as Nd:YAG laser, Argon laser, etc. from the forward end of a laser beam guide of an optical fiber such as an elongated quartz core which is optically connected to a laser source.

Such a non-contact type laser irradiation probe is used in such a manner that it is kept a distance from the tissue so as not to contact the tissue for preventing possible burning of the laser emitting end of the optical fiber. This type of laser probe has no fatal problem and therefore desired effect can be obtained if the laser output is kept constant and the distance from the tissue is kept constant during the laser irradiation. In fact, however, it is quite difficult to keep the distance constant from the tissue because the living tissue moves by itself and it is also difficult for the operator to keep the distance constant by a free hand. Therefore, the effect of laser irradiation onto the tissue cannot be constant or uniform and a serious result is possibly caused onto the patient. This problem is most noticeable when the laser probe is used for laser irradiation treatment through endoscope.

The conventional laser probe has another problem that the divergency angle of laser beam which is emitted from the tip end of the optical fiber into air is as small as 7° to 10° and therefore the irradiation must be repeated to cover the entire area to be irradiated by laser beam and a considerable time is required to complete the irradiation. The probe has a further problem that since the laser is once emitted into air and onto the tissue, 30 to 40% of the emitted laser beam, in general, is backscattered from the surface of the tissue and a serious energy loss is caused.

With respect to protection of the laser emitting end of the optical fiber, i.e., cooling of the emitting end of the fiber and prevention of blood or mucus from entering the end of the fiber in the conventional laser probe, a gas is fed through a space between a sheath tube covering optical fiber and an outer tube covering the sheath tube and discharged outside of the probe to effect cooling of the laser emitting end of the fiber and expelling of blood and mucus. This also involves such a serious problem that a considerable amount of gas is needed to acquire a sufficient cooling effect because a gas generally has rather low cooling ability. For example, when the conventional laser probe of this type is used for irradiation onto an inner wall of stomach, the stomach is filled with a gas and swollen by the gas. This not only gives the patient unpleasantness but sometimes causes perforation in the stomach wall because laser is irradiated on the swollen and thinned stomach wall.

The typical structure of the conventional laser probe suited for hemostasis will now be described referring to FIGS. 9 and 10.

100 designates an optical fiber made for example of quartz covered by sheath 102. The fiber 100 is optically connected to a laser source. An outer tube 106 is coaxially provided around the sheath tube 102 keeping a gap 104 therefrom. An annular tip member 108 is disposed at the forward end of the tube 102 so that the laser emitting end of the optical fiber 100 may not directly contact the tissue. The outer tube 106 is fitted around a stepped portion of the tip member 108 so that the assembly has a smooth or flush surface. The stepped portion of the tip member 108 has two slits 110.

In use of this probe, laser beam irradiation is carried out keeping the probe distanced from the tissue and feeding a gas G through the gap 104 between the sheath tube 102 and the outer tube 106. The gas is guided into the tip member 108 through the slits 110 and discharged from the opening of the forward end of the tip member 108.

This conventional laser probe, however, cannot enlarge the divergency angle determined by the characteristics of the optical fiber 100 itself. Although the tip member 108 is provided and a gas is jetted to prevent blood etc. from entering the laser emitting end of the optical fiber 100 for protection of the probe, this cannot be prevented completely and the treatment is interrupted and serious result is caused when blood or mucus from the tissue enter the emitting end.

It is first consideration of the present invention to provide a medial and surgical laser probe capable of effecting contact irradiation and having improved operating efficiency.

It is another consideration of the present invention to provide a medical and surgical laser probe which is capable of protecting the laser emitting end of the optical fiber by preventing possible burning of the emitting end of the fiber.

It is further consideration of the present invention to provide a medical and surgical probe which is capable of eliminating energy loss due to backscattering of laser beam and capable of effecting irradiation by a reduced power.

It is further consideration of the present invention to provide a medical and surgical laser probe which is capable of enlarging a divergency angle of laser irradiation so as to increase the irradiation area and reducing the time required for irradiation of the entire area to be irradiated.

SUMMARY OF THE INVENTION

According to the present invention, there is provided a medical and surgical laser probe including an optical fiber connected optically to a laser source for emitting laser beam, which comprises a contact member of a laser transmitting material disposed in front of the optical fiber and adapted to be used in contact with the tissue to be irradiated by laser beam, said contact member allowing the laser beam to be transmitted therethrough without causing substantial convergency.

Further according to the present invention, there is provided a medical and surgical laser probe including an optical fiber optically connected to a laser source, a sheath tube covering the fiber, an outer tube coaxially disposed around the sheath tube keeping a gap therefrom and a fluid introducing member provided at a base portion of the probe for letting a fluid pass through the gap, which probe comprises a hollow and cylindrical holder fitted around the forward portion of the sheath tube and engaged with the outer tube to receive the forward end portion thereof; and a contact member made of a laser transmitting material and disposed in front of the forward end of the optical fiber so as to be used in contact with the tissue to be irradiated by laser beam, allowing the laser beam to transmit therethrough without causing any substantial convergency, said contact member being fixed to the holder.

GENERAL BACKGROUND OF THE INVENTION

It is one of the most characteristic feature of the present invention to provide a contact member of laser transmitting material in front of the forward end of the optical fiber so as to allow the probe to be used in contact with the tissue during irradiation. None of the conventional probes are of contact type. Among the conventional laser probes, there is known a probe having a tapered rod member of laser transmitting material disposed at the forward end of the optical fiber so as to converge the laser beam for effecting incision. This type of probe is specialized for the incision but not suited for effecting coagulation, and it is also of a non-contact type and cannot be free from the disadvantages involved in the non-contact type probe.

If irradiation is carried out with the contact member directly contacted with the tissue, especially with the contact member lightly pressed against the tissue following the movement of the tissue, the irradiation effect is not varied by the movement of the living tissue. In addition, it becomes unnecessary to carefully keep the distance between the tissue and the probe and it suffices to lightly press the contact member against the tissue so as not to disengage therefrom. Thus, the operating efficiency is highly improved. This effect is especially noticeable in the endoscopic irradiation.

By the provision of the contact member at the forward end of the optical fiber, it is prevented that blood or mucus enters the laser emitting end of the optical fiber. Thus, burning of the emitting end of the optical fiber can be prevented and possible interruption of medical treatment by irradiation can be avoided.

In the conventional laser probe, it is necessary that blood or mucus be expelled from the emitting end of the optical fiber as well as the emitting end be cooled by feeding a gas. However, according to the present invention, the penetration of blood etc. into the emitting end can be prevented and therefore it suffices to cool the emitting end of the optical fiber which generates a heat due to scattered laser beam. Therefore, only small amount of cooling fluid such as watercan attain the purpose. The cooling water is supplied dropwise from the forward end of the probe. Thus, there can be solved a problem of a pain of the patient or undesired perforation of the tissue due to a gas fed for cooling of the emitting end and expelling of blood etc. involved in the conventional laser probe. The probe of the present invention can also be suitably applied to an organ where any type of gas cannot be used. It is, however, to be noted that a gas may also be used in the present invention as the case may be.

Furthermore, so far as the emitting end of the optical fiber and the tissue are opposite each other, the divergency angle of the optical fiber is determined as 7° to 10° as described above. If the diameter of the laser beam irradiation is small as in the conventional case, the area to be irradiated must be divided and irradiation must be repeated to complete irradiation of the entire area. Thus, it takes a considerable time to complete irradiation. For example, when a vein is required to be closed, such a procedure is necessitated that irradiation is repeated around a blooding opening of the vein so as to effect hemostasis and thereafter the blooding opening is coagulated. For this reason, the contact member has a back formed in a concaved curved face to enlarge the divergency angle and allow the laser beam to be irradiated at an increased divergency angle. As a result, treatment of a wider area can be accomplished by one irradiation. For example, when the vein is required to be closed as mentioned above, it substantially suffices to make irradiation with the contact member being directly pressed against the blooding opening of the vein to accomplish hemostasis.

As to the problem of backscattering which has been inevitable in the non-contact type laser probe can be solved in the present invention which is adapted for contact irradiation. As a result, a laser source of reduced power can be employed, providing economical advantage to the probe.

PREFERRED EMBODIMENT OF THE PRESENT INVENTION

Figure 1:
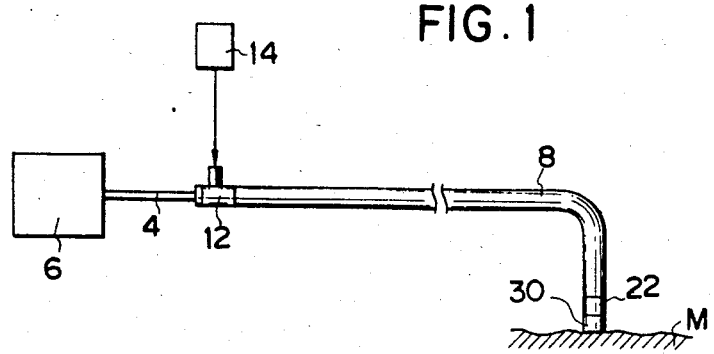
FIG. 1 is an explanatory view of a laser irradiation system according to the present invention.

The invention will now be described in detail referring to the drawings.

Figure 2:
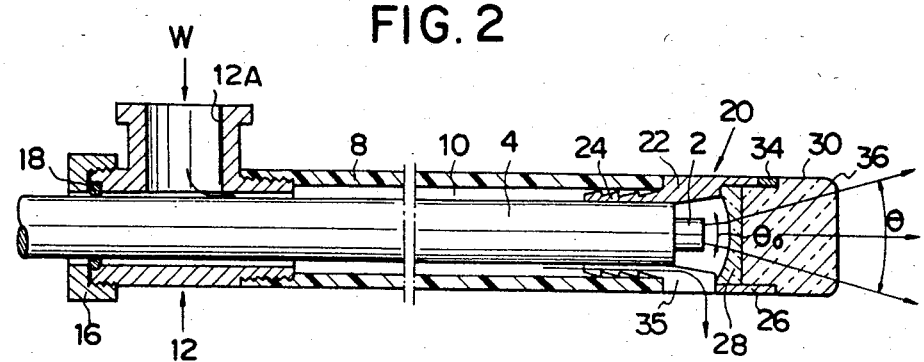
FIG. 2 is a sectional side view of a laser probe according to the present invention.

FIG. 1 is a schematic view of the entire system of the laser irradiation apparatus according to the present invention and FIG. 2 is a sectional view of the detail of a laser probe of the present invention.

Numeral 2 designates an optical fiber made of for example glass or quartz, preferably quartz. The fiber is covered by sheath tube 4 made for example of Teflon (a trade mark of polymer of tetrafluoroethylene manufactured and sold by du Pont). The optical fiber 2 is optically connected to a known laser source 6. Numeral 8 is an outer tube made for example of Teflon and disposed coaxially around the tube 4 keeping a gap 10 therefrom. A T-shaped adaptor 12 of a metallic material is provided at the base portion of the outer tube 8 for letting a fluid such as water W or gas into the gap 10 and water is fed from a water tank 14 or gas holder into an inlet 12A. A cap 16 is threadedly fitted to the rear portion of the adaptor 12 and an O-ring 18 is fitted so as to abut against the tube 4 for constituting water-tight structure for the gap 10.

Figure 3:
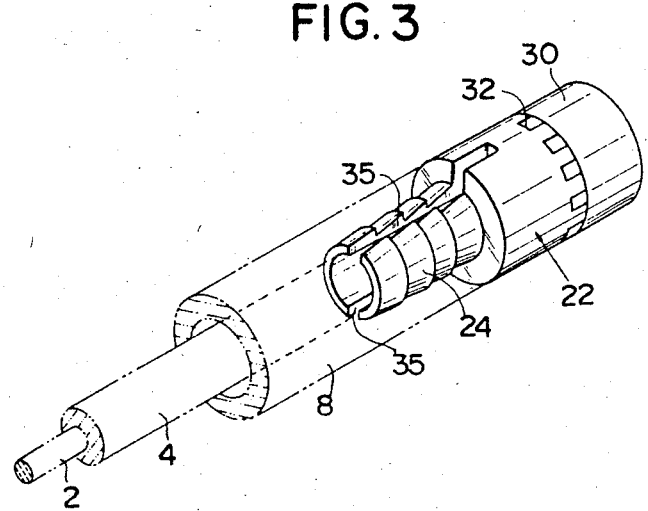
FIG. 3 is a perspective view of the forward end portion of the laser probe of FIG. 2.

A holder 20 made of a metallic material is disposed at the forward end portion of the laser probe. The holder 20 has a body portion 22 whose rear portion is stepped to form a recess around the periphery thereof to provide a fitting portion 24. This fitting portion 24 is tightly fitted between the tube 4 and the outer tube 8. The outer face of the fitting portion 24 has corrugations as shown in FIG. 3 so as to prevent slip out of the outer tube 8 from the fitting portion 24.

The holder 20 has, at the forward portion of the body portion 22 thereof a contact member fixing portion 26 formed with a stepped portion on the inner face thereof. A concaved lens 28 is inserted into the fixing portion 26 and a constant tip 30 having a stepped back of a reduced diameter is fitted in front of the lens. The forward end of the fixing portion 26 has a cutout 32 (FIG. 3). The contact tip 30 is mounted in such a manner that the step is first inserted into the fixing portion 26 and fixed to the holder 20 by an adhesive 34 applied to their faces being in close contact with each other and the cutout 32.

At least one slit, for example two slits 35, 35 are formed on the holder 20 which extend from the rear end of the holder 20 over the fitting portion 24 and the body portion 22 thereof. By these slits 35, the inner space of the holder 20 is communicated with the gap 10 and the outside.

The concaved lens 28 and the contact tip 30 cooperate to provide a contact member of the present invention. They are made of quartz or an artificial sapphire and at least the contact tip 30 is preferably made of an artificial sapphire.

The artificial sapphire is formed into the contact member of the present invention in such a manner than the C-axis of the crystalline structure of the artificial sapphire is disposed along the longitudinal direction of the contact member. The artificial sapphire of the present invention has characteristics as summarized in the following:

| Material/Formula | $Al_2O_3$ |
|---|---|
| Melting Point | 2030–2050° C. |
| Specific Heat | 0.18(25° C.) |
| Thermal Conductivity, g · cal. · cm$^2$ · sec | 0.0016–0.0034(40° C.) |
| Coefficient of Thermal Expansion, $10^{-7} \times$ cm/°C. | 50–67 |
| Elastic Coefficient, $10^{-6} \times$ kg/cm$^2$ | 5.0 |
| Specific Gravity | 4.0 |
| Hardness, Mohs | 9 |
| Compressive Strength, kg/cm$^2$ | about 28000 |
| Tensile Strength, kg/cm$^2$ | about 2000 |
| Index of Refraction | 1.76 |
| Absorption Degree of Water | 0.00 |
| Chemical Characteristic | Acid and Base Proof |
| Appearance | Clear |
| Crystal Form | Hexagonal System |
| Transmittance for YAG Laser | 90% or more |

The artificial sapphire of this kind may be obtained by any suitable means such as a zone melting method or Verneuil method. The Verneuil method is advantageous over the zone melting method in respect with light transmission and therefore Verneuil method is preferably employed to manufacture the artificial sapphire of the present invention. According to this method, the material, i.e., $Al_2O_3$ powder is subjected to melting at a temperature of about 2040° C. and dropped by gravity through a nozzle to allow crystallization to take place.

The artificial sapphire employed for the contact member has such advantages that it is physiologically neutral, has high mechanical strength, high hardness, high laser beam transmission, excellent thermal resistance and low thermal conductivity and is free from tissue adhesion, which are all required for the material of the contact member of the laser probe. In especial, the thermal conductivity of the artificial sapphire is as low as 1/10 of the thermal conductivity of the quartz. This feature enbles the laser probe to be used in contact with the tissue. Heretofore, there have been no laser probe made of an artificial sapphire.

Figure 4:
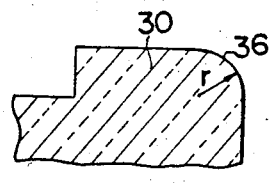
FIG. 4 is an explanatory sectional view showing the configuration of the peripheral portion of the forward end of the contact member.
Figure 7:
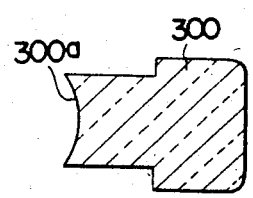
FIG. 7 is an explanatory sectional view of another form of contact member.

The periphery of the forward end face of the contact tip 30 is preferably rounded in a curvature preferably in a circular curvature 36 as shown in FIGS. 2 and 4 (as best shown).

Figure 5:
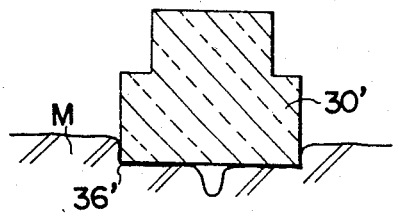
FIG. 5 is an explanatory view showing the peripheral portion of the forward end of the contact member formed in an angular configuration.
Figure 6:
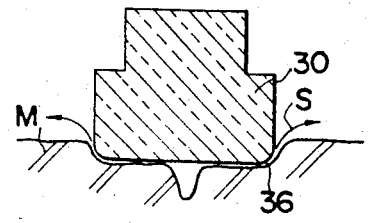
FIG. 6 is an explanatory sectional view showing the expelling of blood being coagulated along the peripheral portion of the forward end of the contact member formed in a rounded configuration.

The contact tip may have an angular, for example right-angle periphery as depicted by 36' of a contact tip 30' in FIG. 5. However, since the angular periphery 36' is strongly pressed against the tissue M, the coagulated blood etc. under the portion of the tissue which is undergoing the pressure by the contact tip 30' cannot flow out so that a desired effect cannot be obtained. In this respect, it is to be noted that with a rounded periphery of the forward end of the contact tip 30, the coagulated blood S can be expelled smoothly as shown in FIG. 6 by the reason not known definitely. The rounding of the periphery of the tip end of the contact tip is also desired because it reduces concentration of stress due to heat generated through contact with the tissue and it is effective to prevent possible breakage of the contact member.

The radius of the curvature 36 is generally within the range of from 0.1 to 0.5 mm and preferably 0.15 to 0.3 mm. If the radius of the curvature is too small, the expelling of the coagulated blood is not carried out smoothly, while if the radius is too large, the effective laser emitting area (area of the forward end face) of the contact tip 30 is reduced and the degree of scattering is increased.

In the embodiment as illustrated, the concave lens 28 is employed to enlarge the divergency angle $\theta_o$ (generally 7° to 10°) of laser beam from the optical fiber 2 and obtain an irradiation angle of $\theta$. Alternatively, a concaved curved face 300a may be formed integrally with a contact tip 300. However, a commercially available concave lens may advantageously be employed to lower the manufacturing cost.

The laser probe of the present invention is used in the manner as described hereinafter.

Referring to FIGS. 1 and 2, laser beam output from the laser source 6 is transmitted through the optical fiber 2 and emitted from the forward end of the optical fiber at a divergency angle $\theta_o$ of 7° to 10°. The laser beam is refracted by the concave lens 28 and thereafter passed through the lens 28 and the contact tip 30 and emitted from the forward end of the contact tip 30 at an angle of 20° to 45°, preferably 25° to 40°.

This emission of laser beam is carried out while keeping the contact tip 30 inserted into a body for example through an endoscope in contact with the tissue M. At this time, water is supplied from the water tank 14 under a pressure as low as it flows only dropwise. The water is fed through the inlet 12A and passed through the gap 10 and the slit 35. The water W passing through the slit 35 enters a space defined by the holder 20, the concave lens 28 and the forward end of the tube 4 to cool the forward end of the optical fiber 2 and thereafter the water is discharged from the slit 35.

The laser probe of the present invention as described above is especially effective for hemostasis of digestive organ.

In this connection, it is to be noted that the contact tip 30, the holder 22 and the outer tube 8 are assembled in such a manner that the outer surfaces thereof constitute a smooth or flush surface to facilitate introduction of the probe into the body for endoscopic treatment. Of course, the outer diameter of the contact tip 30 may be smaller than that of the holder 22, but desired emitting angle $\theta$ cannot be obtained if the diameter of the contact tip 30 is to small. In general, it is preferred that the contact tip 30 have dimensions of FIG. 8 as specified by $1.5 \leq b \leq 5.0$ (mm) and $1.5 \leq e+f \leq 5.0$ (mm).

EXAMPLE

Figure 8:
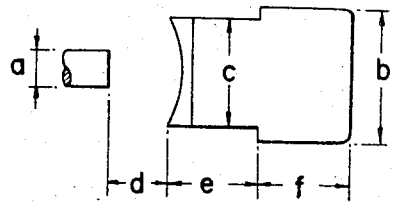
FIG. 8 is an explanatory view showing the dimensions of the laser probe employed in example.
Figure 9:
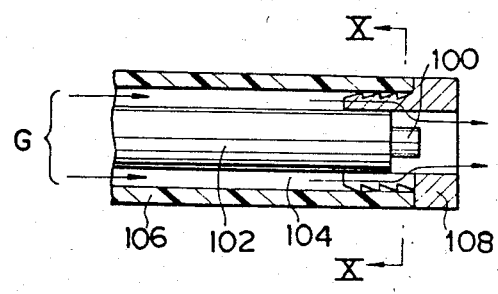
FIG. 9 is a sectional view of the forward end of the conventional non-contact type laser probe.
Figure 10:
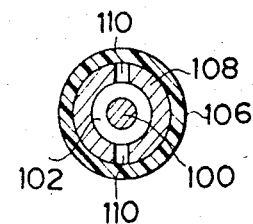
FIG. 10 is a cross sectional view along line X—X of FIG. 9.

The laser probe of the present invention as shown in FIG. 8 which comprises a contact tip and a concave lens having dimensions of $a=0.6$ mm, $b=2.2$, $c=1.8$, $e=f=1.5$ and $d=1.0$ and disposed in the positional relationship as shown in FIG. 8 was used to make laser irradiation treatment for a stomach of a dog and the obtained irradiation effect was inspected. Similar experiment was conducted with respect to the conventional non-contact type laser probe as shown in FIGS. 9 and 10. This non-contact type laser probe employed an optical fiber having an outer diameter of 0.6 mm and was used while keeping a distance of 1.0 mm between the forward end of the probe and the tissue to be irradiated. In both cases, the irradiation time was 1 second. The results with respect to the depth of coagulation made in the tissue are summarized as follow:

|  | Output of Laser (Watt) | | | |
| --- | --- | --- | --- | --- |
|  | 10 W | 20 W | 30 W | 40 W |
| Conventional probe | (No influence) | 0.5 mm | 0.8 mm | 1.3 mm |
| Probe of the Invention | 0.7 mm | 1.5 mm | 2.3 mm | — |

As apparent from the results, the present invention can provide a high irradiation effect as compared with the conventional technique. And desired treatment can be obtained with a reduced laser output.

I claim:

1. A medical and surgical contact laser probe for irradiating human tissue or the like, the laser probe having a forward end and defining a predetermined laser energy radiation area immediately adjacent the laser probe forward end whereby tissue subtended by said area may be irradiated, the laser probe including an optical fiber adapted for connection optically to a source of laser energy at a first end of the optical fiber and probe tip means consisting of laser transmissive material disposed in front of the second end of the optical fiber and means for securing the transmissive material in said front positions, the transmissive material extending from the securing means whereby the securing means remains clear of tissue when the transmissive material of the tip means is brought into contact with said tissue.

2. A medical and surgical laser probe according to claim 1, wherein the transmissive material includes a substantially planar means for contacting the tissue, the peripheral portion of the contacting means being rounded with a curvature.

3. A medical and surgical laser probe according to claim 2, wherein the radius of the curvature is 0.1 mm to 0.5 mm.

4. A medical and surgical laser probe according to claim 1 including means for directing the laser energy, the directing means including a concave back face integrally formed on the transmissive material.

5. A medical and surgical laser probe according to claim 1 including means for directing the laser energy, the directing means including a lens operatively position between the transmissive material and the optical fiber, the lens having a concave rearward surface for receiving laser energy from the optical fiber, the lens being made of laser transmitting material.

6. A medical and surgical laser probe system including an optical fiber optically connected to a laser source, a sheath tube covering the fiber, the sheath tube having a forward end portion, an outer tube coaxially disposed around the sheath tube keeping a gap therefrom and a fluid introducing member provided at a base portion of the probe for letting a fluid pass through the gap, which probe comprises a hollow and cylindrical holder fitted around the forward portion of the sheath tube and engaged with the outer tube to receive the forward end portion thereof; and probe tip means consisting of laser transmissive material disposed in front of the forward end of the optical fiber said holder securing the transmissive material in said front position, the transmissive material extending from the holder whereby the holder remains clear of tissue when the transmissive material of the tip means is brought into contact with said tissue.

7. A medical and surgical laser probe according to claim 6, wherein the outer tube, the holder and the transmissive material are assembled so as to have substantially equal and uniform outside cylindrical diameters whereby the outer tube, the holder, and the transmissive material form a smooth or flush surface as assembled.

8. A medical and surgical laser probe according to claim 6, wherein the transmissive material has, at its rear portion, a stepped portion which is fitted in the holder.

9. A medical and surgical laser probe according to claim 6, wherein the holder has at its rear portion a recess around the periphery thereof which extends from a body portion thereof to form a fitting portion fitted tightly within the gap and has at least one slit extending over the body and fitting portion of the holder along the longitudinal axis of the probe, said slit being communicated with the gap, a laser emitting end of the optical fiber and the outside of the probe.

* * * * *

REEXAMINATION CERTIFICATE (1039th)
United States Patent [19]

Daikuzono

[11] B1 4,592,353

[45] Certificate Issued Apr. 18, 1989

[54] MEDICAL AND SURGICAL LASER PROBE

[75] Inventor: Norio Daikuzono, Ichikawa, Japan

[73] Assignee: Surgical Laser Technologies Ohio, Inc., Cincinnati, Ohio

Reexamination Request:
No. 90/001,247, May 19, 1987

Reexamination Certificate for:
Patent No.: 4,592,353
Issued: Jun. 3, 1986
Appl. No.: 612,674
Filed: May 22, 1984

[51] Int. Cl.⁴ ............................................. A61B 17/36
[52] U.S. Cl. .............................. 128/303.1; 219/121 L; 219/121 R
[58] Field of Search .................. 128/303.1, 395–398; 219/121 L, 121 LP, 121 LR, 121 LQ

[56] References Cited
U.S. PATENT DOCUMENTS

| | | | |
|---|---|---|---|
| 3,236,707 | 2/1966 | Lins | 219/121 LP X |
| 3,821,510 | 6/1974 | Muncheryan | 219/121 L |
| 3,843,865 | 10/1974 | Nath | 219/121 L |
| 3,910,276 | 10/1975 | Polanyi et al. | 128/303.1 |
| 4,069,080 | 1/1978 | Osborne | 219/121 LR X |
| 4,233,493 | 11/1980 | Nath | 128/303.1 X |
| 4,273,109 | 6/1981 | Enderby | 128/6 |
| 4,313,431 | 2/1982 | Frank | 128/303.1 X |
| 4,519,390 | 5/1985 | Horne | 128/303.1 |
| 4,539,987 | 9/1985 | Nath et al. | 128/303.1 |
| 4,633,872 | 1/1987 | Chaffee et al. | 128/303.1 |
| 4,733,660 | 3/1988 | Itzkan | 128/303.1 |

FOREIGN PATENT DOCUMENTS 2717421 11/1978 Fed. Rep. of Germany ... 128/303.1
2023004 12/1979 United Kingdom .

*Primary Examiner*—Lee S. Cohen

[57] ABSTRACT

A medical and surgical laser probe which is provided with a contact member made of a laser transmitting material in front of a forward end of a laser guide so as to enable the probe to be used in contact with the tissue. The contact member has a specified configuration which causes no substantial convergency so as to be specially adapted coagulation treatment. With the contact member of the present invention, the coagulation treatment can be carried out effectively.

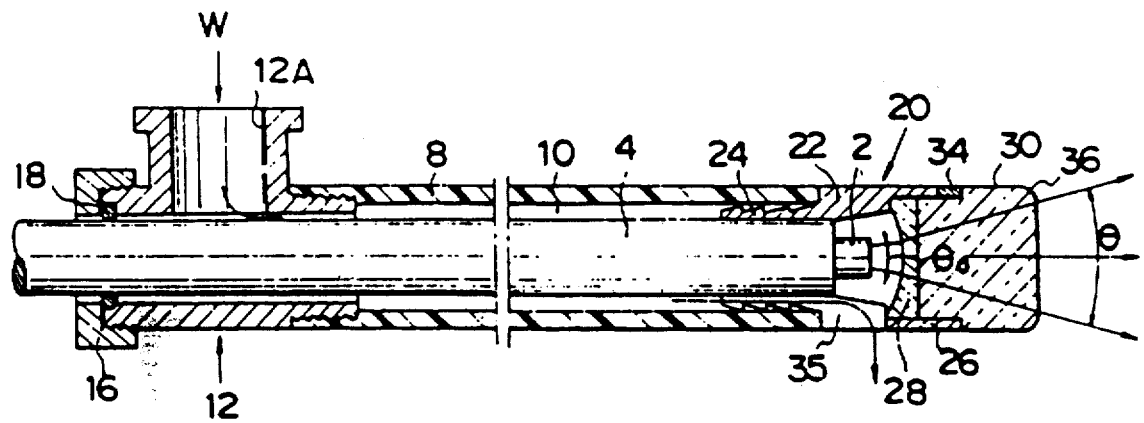

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 6–9 is confirmed.

Claim 1 is determined to be patentable as amended.

Claims 2–5, dependent on an amended claim, are determined to be patentable.

New claims 10–13 are added and determined to be patentable.

1. A medical and surgical contact laser probe for irradiating human tissue or the like, the laser probe having a forward end and defining a predetermined laser energy radiation area immediately adjacent the laser probe forward end whereby tissue subtended by said area may be irradiated, the laser probe including *a tip means and means for transmitting laser energy from a source of laser energy to the tip means, said tip means to be positioned to perform a surgical procedure on or within a patient, said transmitting means including a laser optical fiber adapted for insertion through an endoscope, the laser optical fiber having a first end adapted for connection to the source of laser energy,* [an optical fiber adapted for connection optically to a source of laser energy at a first end of the optical fiber and], *the* probe tip means consisting of laser transmissive material disposed in front of the second end of the optical fiber and means for securing the transmissive material in said front [positions] *position*, the transmissive material extending from the securing means whereby the securing means remains clear of tissue when the transmissive material of the tip means is brought into contact with said tissue.

10. *A medical and surgical contact laser probe for irradiating human tissue including endoscopic and interstitial procedures, the laser probe having a forward end and defining a predetermined laser energy radiation area immediately adjacent the laser probe forward end whereby tissue subtended by said area may be irradiated, the laser probe including an optical fiber adapted for connection optically to a source of laser energy at a first end of the optical fiber and probe tip means comprising laser transmissive material disposed in front of the second end of the optical fiber and means for securing the transmissive material in said front position; a laser energy inlet region defined on the transmissive material where the laser energy from the optical fiber enters said material; the transmissive material extending from the securing means whereby the securing means remains clear of tissue when the transmissive material of the tip means is brought into contact with said tissue; means for cooling the laser probe, said cooling means including means for providing a restricted liquid fluid flow in the probe whereby a minimum volume of fluid is discharged from the probe tip means.*

11. *A medical and surgical contact laser probe for irradiating human tissue including endoscopic and interstitial procedures, the laser probe having a forward end and defining a predetermined laser energy radiation area immediately adjacent the laser probe forward end whereby tissue subtended by said area may be irradiated, the laser probe including an optical fiber having first and second opposed ends, said optical fiber adapted for connection optically to a source of laser energy at a first end of the optical fiber and probe tip means comprising laser transmissive material disposed in front of the second end of the optical fiber and means for securing the transmissive material in said front position; a laser energy inlet region defined on the transmissive material where the laser energy from the optical fiber enters said material; the transmissive material extending from the securing means whereby the securing means remains clear of tissue when the transmissive material of the tip means is brought into contact with said tissue; means for cooling the laser probe, said cooling means including means for maintaining a liquid coolant in contact with the second end of the optical fiber and with the inlet region of the transmissive material whereby heat generated due to losses in coupling the laser energy from the fiber to the tip means can be dissipated.*

12. *The medical and surgical contact laser probe of claim 11 wherein the liquid coolant maintaining means includes means for enclosing the second fiber end and inlet region thereby defining a substantially liquid tight coolant chamber therearound; the enclosing means including an aperture through which liquid coolant can pass from the coolant chamber at a predetermined flow rate; means for replenishing the coolant in the chamber whereby a continuous limited flow of coolant is maintained adjacent the second fiber end and the inlet region.*

13. *A medical and surgical contact laser probe for irradiating human tissue including endoscopic and interstitial procedures, the laser probe having a forward end and defining a predetermined laser energy radiation area immediately adjacent the laser probe forward end whereby tissue subtended by said area may be irradiated, the laser probe including an optical fiber adapted for connection optically to a source of laser energy at a first end of the optical fiber and probe tip means consisting of laser transmissive material disposed in front of the second end of the optical fiber and means for securing the transmissive material in said front positions, the transmissive material extending from the securing means whereby the securing means remains clear of tissue when the transmissive material of the tip means is brought into contact with said tissue; means for cooling the tip means, said cooling means including a sheath disposed generally coaxially around the optical fiber thereby defining a fluid gap therebetween, means for sealing the sheath in liquid-tight engagement to the tip means, means for introducing liquid into the gap, fluid flow means for permitting a predetermined restricted flow of fluid from the gap, said fluid flow means comprising an aperture in one of said sheath and transmissive material securing means, said aperture being in fluid communication with said gap whereby a minimum volume of fluid is discharged from the probe tip means.*

* * * * *